United States Patent [19]
Misaki et al.

[11] Patent Number: 5,602,111
[45] Date of Patent: Feb. 11, 1997

[54] AGENT FOR INDUCING PHYTOALEXIN AND METHOD FOR INDUCING PHYTOALEXIN

[75] Inventors: Akira Misaki, Ashiya; Keiji Sekiya, Takatsuki; Kazuhiko Yamatoya, Izumisano, all of Japan

[73] Assignee: Dainippon Pharmaceutical Co., Ltd., Osaka, Japan

[21] Appl. No.: 343,453

[22] PCT Filed: May 28, 1993

[86] PCT No.: PCT/JP93/00728

§ 371 Date: Nov. 28, 1994

§ 102(e) Date: Nov. 28, 1994

[30] Foreign Application Priority Data

May 29, 1992 [JP] Japan ................................ 4-163501

[51] Int. Cl.$^6$ .......................... A61K 31/715; C07G 3/00; C09B 47/04
[52] U.S. Cl. ........................ 514/54; 536/4.1; 536/123.12; 536/128; 514/449
[58] Field of Search ..................... 424/195.1; 514/449, 514/54; 536/123.12, 4.1, 128

[56] References Cited

FOREIGN PATENT DOCUMENTS

| | | |
|---|---|---|
| 1332880 | 10/1987 | Canada. |
| 63-215606 | 9/1983 | Japan. |
| 60-190800 | 9/1985 | Japan. |

OTHER PUBLICATIONS

International Search Report for International Appln. No. PCT/JP93/00728 dated Aug. 13, 1993.

*Primary Examiner*—John W. Rollins
*Attorney, Agent, or Firm*—Varndell Legal Group

[57] ABSTRACT

An agent for inducing a phytoalexin comprising a xyloglucan-oligosaccharide as an active ingredient thereof and a method for inducing a phytoalexin in a plant body comprising an application of a xyloglucan-oligosaccharide to the plant. The present invention is useful for promoting growth of a plant and maintaining freshness of a plant while a crop has been grown, or a vegetable or a fruit has been transported and/or stored.

7 Claims, No Drawings

AGENT FOR INDUCING PHYTOALEXIN AND METHOD FOR INDUCING PHYTOALEXIN

TECHNICAL FIELD

The present invention relates to an agent for inducing a phytoalexin and a method for inducing a phytoalexin in a plant. More particularly, the present invention relates to an agent for inducing a phytoalexin comprising a xyloglucan-oligosaccharide as an active ingredient thereof, which is useful as a biotic pesticide, an agent for maintaining freshness of a plant, a coating agent for a seed, a capsule material for preparing a synthetic seed, an agent for maintaining freshness of a chopped vegetable, or the like, and a method for inducing a phytoalexin, which is useful for promoting growth of a plant or for maintaining freshness of a plant, while a crop has been grown, or a vegetable or a fruit has been transported and/or stored.

BACKGROUND ART

Large quantities of agricultural chemicals have now been used to prevent microbial infections while crops are cultivated. For example, seeds are treated with chemicals before being sowed in order to promote good germination and furthermore, chemicals are spread in order to reduce damages caused by microbial infections while plants have grown up and bear fruits. However, there are various problems in respect of safety, such as influences on human bodies exerted by the chemicals remaining on the crop, and the environmental pollution by diffused chemicals.

It has been known that a plant has various defense systems against infections originally, and that when a plant is infected with a microorganism, an antimicrobial substance which is not present in normal tissue is induced for resisting the infection. This antimicrobial substance is referred to as a phytoalexin. A phytoalexin is induced by a cell component of a microorganism, a fragment of a polysaccharide which construct the cell wall of the plant infected by a microorganism, or the like. This substance which induces a phytoalexin is referred to as an elicitor.

Moreover, it is considered that the elicitor activity not only induces a phytoalexin but also participates in induction of an enzyme inhibitory substance such as a protease inhibitor, and in production of a plant hormone, e.g., ethylene, and the like.

A fragment of β-glucan derived from the cell wall of *Phytophthora megasperma* (Janice K. Sharp et al, Journal of Biological Chemistry, Vol. 259, No. 18, 11312–11320, 1984), and oligogalacuturonic acid, which is a fragment of a pectin, (Peter Albersheim et al, Scientific American, Vol. 253, 44–50, 1985; Akira Misaki et al, Agricultural and Biological Chemistry, Vol. 54, No. 6, 1477–1484, 1990) are known as substances with elicitor activity. It is considered that a substance with the elicitor activity may be used as a biotic pesticide. However, it is difficult to put the currently known substances with the elicitor activity into practical use, because there are various problems, such as cost, the amount which can be supplied or the preparation procedure of the polysaccharide as a raw material.

On the other hand, it has been known that a xyloglucan-oligosaccharide which is obtained by degradation of a xyloglucan, i.e., a polysaccharide which constructs the cell wall of a higher plant, participates in growth of a plant. The following facts have been known; that a pentasaccharide, a heptasaccharide or a nonasaccharide of a xyloglucan-oligosaccharide activates endo-1,4-β-glucanase in a plant (Vladimir Farkas et al, Carbohydrate Research, Vol. 184, 213–219, 1988), that a heptasaccharide, an octasaccharide, or a nonasaccharide of a xyloglucan-oligosaccharide promotes elongation of a slice of pea-hypocotyl (Gordon J. McDougall et al, Plant Physiology, Vol. 93, 1042–1048, 1990), and that a nonasaccharide of a xyloglucan-oligosaccharide has an inhibitory effect against elongation caused by auxin (Gordon J. McDougall et al, Plant Physiology, Vol. 89, p. 883–887, 1989). However, the elicitor activity of a xyloglucan-oligosaccharide has not been heretofore known at all.

DISCLOSURE OF THE INVENTION

The present inventors found that a xyloglucan-oligoaccharide has an elicitor activity and is notably useful as an agent for inducing a phytoalexin, and accomplished the present invention.

The present invention relates to an agent for inducing a phytoalexin comprising xyloglucan-inducing oligosaccharide as an active ingredient and a method for inducing a phytoalexin in a plant comprising an application of a xyloglucan-oligosaccharide to the plant.

A xyloglucan-oligosacchride which is the active ingredient of the agent for inducing a phytoalexin of the present invention is obtained by degrading a xyloglucan using an enzyme, an acid, or the like. A xyloglucan is a polysaccharide that is known to exist generally in primary cell wall of a monocotyledon and a dicotyledon. It also exists in Tamarind, soybean, mung bean, kidney bean, rice plant, barley, apple, and the like.

The xyloglucan-oligosaccharide which is the active ingredient of the agent for inducing a phytoalexin of the present invention is preferably one which is obtained by degrading a polysaccharide derived from Tamarind seed, more preferably, the xyloglucan-oligosaccharide which is obtained by degrading the polysaccharide derived from Tamarind seed and has the following physical properties:

① the viscosity of a 10% by weight aqueous solution thereof measured at 25° C. by means of a BL model viscometer at 30 rpm being not more than 10 cps, ② negative with an iodine color reaction, ③ the constituent sugar ratio (glucose/xylose/galactose) of 4/3.8-2/2-0, ④ the mean molecular weight of 600–3000 and ⑤ 10–15% by weight of a heptasaccharide, 30–40% by weight of a octasaccharide and 35–45% by weight of a nonasaccharide being contained therin.

The polysacchride from Tamarind seed has a structure in which xylose and galactose bind to a main chain consisting of β-1,4 glucan, as a side chain. The polysacchride is utilized as a thickner for foods for example, sauce and ice cream.

A method for preparing a xyloglucan-oligosaccharide from said polysaccharide is for example, enzymatic degradation or acid hydrolysis.

In case of the enzymatic degradation is carried out a plant tissue hydrolyzing enzyme that has β-1,4-glucanase activity is employed. The reaction conditions such as an amount to be added, pH, temperature, and reaction time are determined suitably depending on the enzyme employed. For example, in case that cellulase is employed as the enzyme, the amount of the enzyme to be added is 0.5–2.0% by weight of the amount of the saccharide, and the reaction is carried out at pH 3–7, for 5–96 hours, at 30°–60° C. After terminating the reaction, the enzyme is inactivated. The product is purified by a method such as chromatography, if desired, and then lyophilized to give a xyloglucan-oligosacchride.

Thus obtained xyloglucan-oligosaccharide has the following physical properties:

Viscosity

The xyloglucan-oligosacchride is heated at 80° C. for 10 minutes together with water to give a 10% by weight aqueous solution. Viscosity of thus obtained solution is measured at 25° C. by means of a Brookfield model viscometer at 30 rpm. The viscosity of the above solution is not more than 10 cps.

Iodine color reaction

When a solution of potassium iodide (0.1M) is added to the above-described solution to make the final concentration of potassium iodide to be 0.002M, thus obtained mixture is not colored.

Constituent sugar ratio

The above aqueous solution is diluted to give a 1% by weight aqueous solution. The same amount of 2N sulfuric acid is added thereto. The resulting mixture is heated at 100° C. for 6 hours. Thus obtained solution is neutralized with an aqueous solution of barium hydroxide and desalted. The desalting is achieved by subjecting the solution to Toyopack IC SP (Trade name, made by TOSOH CORPORATION, Japan). The sample is subjected to DEAE cellulose, and then filtered with a 45 μm membrane filter. The desalted solution is concentrated and subjected to a high performance liquid chromatography (column: Shodex Sugar SP0810 (Trade name, made by SHOWA DENKO K.K., Japan)→SP0810, eluate: distilled water, temperature: 65° C., flow rate: 1.0 ml/min, detector: RI). According to the investigation using the high performance liquid chromatography, the constituent sugar ratio (glucose/xylose/galactose) is 4/3.5-2/2-0.

Mean molecular weight

The above-described xyloglucan-oligosacchride is subjected to a high performance liquid chromatography (coloumn: KS800P (Trade name, made by SHOWA DENKO K.K. Japan)→KS805 (Trade name, made by SHOWA DENKO K.K.)→KS802 (Trade name, made by SHOWA DENKO K.k.), eluate: distilled water, temperature: 60° C., flow rate: 1.0 ml/min, detector: RI). The determined mean molecular weight is 600–3000.

Composition of the xyloglucan-oligosaccharide

A fragment of the xyloglucan-oligosaccharide is obtained by the procedure which is described bellow in Preparation Example 1. The composition of the fragment is determined. It is found that the above xyloglucan-oligosaccharide contains 10–15% by weight of a heptasaccharide, 30–40% by weight of an octasaccharide, and 35–45% by weight of a nonasaccharide. The heptasaccharide has a basic structure where three molecules of α-xylose bind to β-1,4 linked four glucose residues at three of the positions 6 thereof. Further, the octasaccharide has a structure where one molecule of galactose binds to one of the above-mentioned xylose of the heptasaccharide via β-1,2-linkage, and the nonasaccharide has a structure where two molecules of galactose bind to the two positions of the above-mentioned xylose of the heptasaccharide via β-1,2-linkage.

As to an activity to induce a phytoalexin, or elicitor activity of the xyloglucan-oligosaccharide which is the active ingredient of the agent for inducing a phytoalexin of the present invention, is explained by means of the following Test Example.

TEST EXAMPLE

Determination of an Elicitor Activity

Cotyledons of soybeans (Tamahomare) were collected on day 8 after sowing. The cotyledons were washed with running water for 5 minutes and further, with distilled water, and then the water was wiped off. Five petri dishes on each of which a wet filter paper was laid were prepared. The reverse side of the cotyledons was sliced off by 1 mm in width with a razor and set on the Petri dishes. Ten slices were set on each Petri dish. For a control group, a drop (90 μl) of 5 mM acetate buffer (pH 6.0) containing 0.02 w/v% streptomycin sulfate was added onto each cotyledon. For a test group, the drop (90 μl) of 5 mM acetate buffer (pH 6.0) containing 0.02 w/v% streptomycin sulfate and 50 μg of a xyloglucan-oligosaccharide prepared by the method described in Preparation Example 1 bellow, i.e., XGO-7, XGO-8, XGO-9 or XGO was added onto each cotyledon. The Petri dishes were covered with lids and allowed to stand at 25° C. for 24 hours in a dark place.

The ten slices of cotyledons were put into a test tube and then 10 ml of distilled water was added thereto. After the tube was vigorously stirred for 2 minutes, the solution was filtered with a membrane-filter, and distilled water was added to the filtrate to give a 10 ml of sample solution. The amount of glyceollin, which is a phytoalexin was determined by measuring absorbance at 286 nm of the sample solution. The value obtained by subtracting the absorbance of the control group from that of the test group was represented as the elicitor activity. The results are shown in Table 1.

TABLE 1

|  | Amount of Glyceollin | Elicitor Activity |
| --- | --- | --- |
| Control group | 0.222 | 0.000 |
| Test group |  |  |
| XGO-7 | 0.502 | 0.280 |
| XGO-8 | 0.611 | 0.389 |
| XGO-9 | 0.457 | 0.235 |
| XGO | 1.715 | 1.493 |

As is clear form the results shwon in Table 1, it was confirmed that the xyloglucan-oligosaccharide has the elicitor activity.

Although the xyloglucan-oligosaccharide can be used alone as an agent for inducing a phytoalexin, it may be used as a mixture with a conventional solid carrier, a liquid carrier, a surfactant, and/or the other supplemental materials for preparation. These are prepared to formulate an emulsion, water-dispersible powder, a suspension, a granule, a liquid, or the like.

In case of being used as a biotic pesticide, the preparation contains 0.001–30% by weight, preferably 0.01–0.5% by weight of a xyloglucan-oligosaccharide as an active ingredient. In case of being used as a coating material or a liquid for immersion, the preparation contains 0.01–30% by weight, preferably 0.1–15% by weight of a xyloglucan-oligosaccharide as an active ingredient. In case of being used as a capsule material for a synthetic seed, the preparation contains 0.01–5% by weight, preferabely 0.1–1% by weight of a xyloglucan-oligosaccharide as an active ingredient.

A solid carrier is for example, mineral powder such as calcium carbonate or diatomaceous earth, a high molecular weight polysaccharide such as starch or crystalline cellulose, or the like. A liquid carrier is for example, methanol, ethanol, water, or the like.

A surfactant which is employed for emulsifying, suspending, or moistening-spreading is for example, a salt of alkyl sulfate ester, a sorbitane ester of a fatty acid, or the like.

The other supplemental agent for preparation is for example, algin, xanthan gum, or the like.

The amount of the agent for inducing a phytoalexin of the present invention employed depends on the weather condition, the preparation form, the season for application, the method of application, the place to be applied, the objective crop, the kind of the object, or the like. In case of being used as a biotic pesticide, the amount of the inducer employed ranges between 0.0001 and 1% by weight of a plant body, wherein the agent for inducing a phytoalexin of the present invention is applied as it is or after dilution with water or the like to soil or to liquid fertilizer for hydroponics. In case of being sprinkled, the amount of the agent for inducing a phytoalexin of the prsent invention to be employed is 10–1000 liter per 10 aru of the farm where a crop is growing. The agent for inducing a phytoalexin of the present invention can be used as a mixture with an agent for plant growth, a herbicide, a pesticide, a miticide, a nematicide, a fertilizer, a soil improving agent, or the like. The agent for inducing a phytoalexin of the present invention can be applied to the same plant body several times with various intervals.

Since a xyloglucan-oligosaccharide has the elicitor activity as mentioned above, a phytoalexin can be induced in a plant by applying the xyloglucan-oligosccharide to the plant.

This application of a xyloglucan-oligosaccharide to a plant can be carried out by way of the following procedure;

mixing a xyloglucan-oligosaccharide into the soil where a plant is grown or the substitutes therefor, for example, a liquid fertilizer or a hydroponic apparatus for hydroponics;

sprinkling a xyloglucan-oligosaccharide while a plant is grown:

coating a seed of a plant with a xylogulucan-oligosaccharide by a procedure such as immersion, spraying, or the like;

coating a plant itself, for example, whole vegetable or chopped vegetable with a xyloglucan-oligosaccharide by a process such as immersion, spraying, or the like;

preparing a capsule of a synthetic seed by way of mixing an adventive embryo of a plant with a xyloglucan-oligasaccharide, and, if necessary, with added nutrients and coating the resulting mixture with a water-soluble polymer such as sodium alginate, or the like.

Induction of a phytoalexin by applying a xyloglucan-oligosaccharide to a plant as mentioned above, results in reduction of withering caused by a pathogen. Accordingly, the growth of the plant can be promoted, and freshness of a crop such as a vegetable can be maintained.

BEST MODE FOR CARRYING OUT THE INVENTION

The present invention is more specifically explained by means of the following Examples.

PREPARATION EXAMPLE 1

(1) Preparation of a xyloglucan

In 20 ml of 60% by volume ethanol aqueous solution was suspended 2.5 g of a polysaccharide from Tamarind seeds (made by DAINIPPON PHARMACEUTICAL CO., LTD.). The seeds swelled sufficiently in the ethanol solution. This suspension was gradually poured into 500 ml of water with stirring by a stirrer, followed by heating at 75° C. for 15 minutes with stirring. This mixture was centrifuged at 10000 rpm for 15 minutes to remove water-insoluble impurities. The supernatant was gradually poured into 100 ml of ethanol with stirring vigorously to give crude xyloglucan as a precipitate. This mixture was centrifuged at 10000 rpm for 15 minutes to remove liposoluble impurities. The precipitate obtained was washed with 67% by volume ethanol aqueous solution, 80% by volume ethanol aqueous solution, 100% ethanol, 50% by volume ethanol, 50% by volume acetone, and 100% acetone successively to be dehydrated. The dehydrated precipitate was dried to give 2.11 g of purified xyloglucan.

(2) Preparation of a xyloglucan-oligosaccharide

Six hundred mg -of purified xyloglucan prepared as described in the above (1) allowed to react with 24 mg of Cellulase Onozuka (Trade name, made by YAKULT HONSHA CO., LTD.) at 37° C. for 72 hours at pH 4.0 in 0.02M acetate buffer. The reaction mixture was heated on a boiling water bath for 3 minutes to inactivate the enzyme. Thus obtained mixture was subjected to AG501-X8 resin (Trade name, made by Bio-Rad Laboratories) and then, concentrated by using a rotary evaporator. The resulting product was freeze-dried to give 500 mg of a xyloglucan-oligosaccharide (referred to as XGO).

After dispersing 500 mg of the above XGO into 5 ml of distilled water, the dispersion was subjected to ultrasonication to dissolve the XGO. This solution was centrifuged at 3000 rpm for 5 minutes to remove a precipitate. The supernatant (4 ml) was subjected to a P2 (Trade name: Bio-Gel P2, made by Bio-Rad Laboratories (ø5 cm×90 cm)) - P4 (Trade name: Bio-Gel P4, made by Bio-Rad Laboratories (ø4 cm×186 cm)) connected column. The flow rate was set at 50 ml/hour. The initial 1200 ml eluate was collected as a drain in a measuring cylinder, and then the following eluate was collected every 6 ml/tube fractions by means of a fraction collector. The eluate was fractionated to give 396 fractions, each of which was tested by a phenolic sulfate method and 8 peaks could be found. The yield of each peak was as follows: peak 1: 4.6 mg, peak 2: 5.5 mg, peak 3: 105.6 mg, peak 4: 87.2 mg, peak 5: 35.9 mg, peak 6: 7.0 mg, peak 7: 6.9 mg and peak 8: 4.8 mg.

Each peak fraction, and as standards, a heptasaccharide and a nonasaccharide of a xyloglucan were subjected to HPTLC (developer: n-butanol/ethanol/water=5/5/4). It was confirmed that peak 3 was a nonasaccharide of a xyloglucan (reffered to as XGO-9), peak 4 was an octasaccharide of a xyloglucan (reffered to as XGO-8) and peak 5 was a heptasaccharide of a xyloglucan (reffered to as XGO-7), respectively, according to the investigation using the HPTLC.

EXAMPLE 1

Biotic Pesticide

On a glass container in which a wool-mat made of synthetic resin was set, were sowed 50 grains of seed of white radish sprout. One hundred ml of tap water was added to the container. For a test group, 0.1 mg of the above-described xyloglucan-oligasaccharide (XGO) was added thereto. They were grown at 25° C. for 6 days in total, that is, for 4 days in the dark and for 2 days in the light. The results are shown in Table 2.

TABLE 2

|  | Length of stem (%) | Withering (%) |
| --- | --- | --- |
| Control group | 82 | 15 |
| Test group (XGO added) | 120 | 1 |

As is clear from the results shown in Table 2, regarding the test group wherein the xyloglucan-oligosaccharide was added thereto, the better growth was observed, and in addition, withering, the cause of which was considered to be pathogenic microorganism, decreased remarkably.

EXAMPLE 2

Maintenance of Freshness of a Plant

Seeds of sunny lettuce were sowed on a wool mat. They were grown in a liquid fertilizer containing 0.15 w/v% of DAIKINHAUSU HIRYO No. 1 and 0.1 w/v% of DAIKINHAUSU HIRYO No. 2 at 23° C. under 5000 lux light for 10 days to cause germination and growth of seedlings. Thereafter, the seedlings were planted into an apparatus for hydroponics and grown at 23° C. under 3000 lux light for 1 month. For a test group, the liquid fertilizer and the apparatus for hydroponics contained 0.01, 0.05 or 0.1 w/v% of the above xyloglucan oligosaccharide (XGO).

After growing, weight of each of the obtained sunny lettuce was measured. Each lettuce was put into a vinyl bag which was partly opened and kept at 5° C. for 5 days. The weight of each of the lettuce was then measured and browning thereof was examined. The results are shown in Table 3.

TABLE 3

|  | Amount of transpirated water* (% by weight) | Browning** |
| --- | --- | --- |
| Control group | 18 | +++ |
| Test group |  |  |
| 0.01% XGO added | 14 | + |
| 0.05% XGO added | 10 | − |
| 0.1% XGO added | 9 | − |

*Amount of transpired water (%) =
$$\frac{\text{(Initial weight)} - \text{(Weight on day 5)}}{\text{Initial weight}} \times 100$$

**Browning:
− No browning
+ Not more than 25% browning (number)
++ 25–50% browning (number)
+++ Not less than 50% browning (number)

As is clear from the results shown in Table 3, the amount of transpirated water was smaller, and less browning occurred in the test group wherein the xyloglucan-oligosaccharide was added, therefore the freshness was well maintained in the test group.

EXAMPLE 3

Coating of Seeds

To a 15 w/v% aqueous solution of a xyloglucan-oligosaccharide (XGO) were added 40 ml of seeds of tomato. The mixture was stirred gently for 10 minutes. The seeds were taken up and air-dried to give the tomato seeds coated with the above xyloglucan-oligosacchride. Thus obtained tomato seeds coated with XGO were used for a test group. As a control group, the tomato seeds without any treatment were employed.

These tomato seeds were sowed onto a vermiculite nursery and watered for germination. Ten days later, the young seedlings were potted with vermiculite into pots made of polyethylene and raised. Thirty days later since the day when potting was practiced, the tomato plants were planted on a farm to which an organic compound fertilizer was applied. The appearance and the yield of the tomatos were examined. The results are shown in Table 4.

TABLE 4

|  | Appearance* | Yield per root (g) |
| --- | --- | --- |
| Control group | + | 2200 |
| Test group (XGO added) | − | 2600 |

*Appearance:
− No damage
+ Damaged by pest insects

As is clear from the results shown in Table 4, less visit by a pest insect occured and the higher yield was obtained in the test group wherein the xyloglucan-oligosaccharide was added.

EXAMPLE 4

Maintenance of Freshness of Chopped Vegetables

Chopped vegetables were prepared by shredding cabbage by means of a slicer and chopping lettuce into 3 cm square pieces.

Each of these was immersed in a 10 w/v% aqueous solution of a xyloglucan-oligosaccharide (XGO) to be test groups. Chopped vegetables which were not treated were employed as control groups. After removing water, the vegetables were allowed to stand at room temperature. Successive changes brought on these vegetables were observed. The results are shown in Table 5.

TABLE 5

|  | Browning* | | | |
| --- | --- | --- | --- | --- |
|  | 10 hr | 24 hr | 48 hr | 72 hr |
| Cabbage control group | − | + | ++ | ++ |
| Cabbage test group (XGO added) | − | − | − | − |
| Lettuce control group | ++ | ++ | ++ | ++ |
| Lettuce test group (XGO added) | − | − | − | − |

*Browning;
− No browing
+ A little browning
++ Browning

As is clear from the results shown in Table 5, in the test group wherein the xyloglucan-oligosaccharide was added, less browning occured, and the chopped vegetables kept their good states for a long time.

INDUSTRIAL APPLICABILITY

The agent for inducing a phytoalexin of the present invention can be used as a biotic pesticide, an agent for maintaining freshness of a plant, a coating agent for a seed, a capsule material for preparing a synthetic seed, and an agent for maintaining freshness of a chopped vegetable, while a crop has been grown, or a vegetable or a fruit is transported and/or stored. By using the method for inducing a phytoalexin of the present invention, growth of a plant can be promoted, and the freshness of a plant can be maintained while a crop has been grown, or a vegetable or a fruit has been transported and/or stored.

We claim:

1. A composition for inducing a phytoalexin comprising an effective amount of a xyloglucan-oligosaccharide for inducing said phytoalexin obtained by degrading a polysaccharide derived from Tamarind seed and has the following physical properties:

① a viscosity of a 10% by weight aqueous solution of the oligosaccharide measured at 25° C. by means of a BL model viscometer at 30 rpm being not more than 10 cps, ② negative with an iodine color reaction, ③ a constituent sugar ratio (glucose/xylose/galactose) of 4/3.5-2/2-0, ④ a mean molecular weight of 600–3000, and ⑤ 10–15% by weight of a heptasaccharide, 30–40% by weight of an octasaccharide and 35–45% by weight of a nonasaccharide being contained therein, and a suitable carrier.

2. A method for inducing a phytoalexin in a plant comprising applying an effective amount of a xyloglucan-oligosaccharide to the plant for inducing the phytoalexin, said xyloglucan-oligosaccharide being obtained by degrading a polysaccharide derived from Tamarind seed and having the following physical properties:

① a viscosity of a 10% by weight aqueous solution of the oligosaccharide measured at 25° C. by means of a BL model viscometer at 30 rpm being not more than 10 cps, ② negative with an iodine color reaction, ③ a constituent sugar ratio (glucose/xylose/galactose) of 4/3.5-2/2-0, ④ a mean molecular weight of 600–3000 and ⑤ 10–15% by weight of a heptasaccharide, 30–40% by weight of an octasaccharide and 35–45% by weight of a nonasaccharide being contained therein.

3. The method according to claim 2, wherein the application of the xyloglucan-oligosaccharide to the plant is carried out by having a xyloglucan-oligosaccharide contained in a soil or a substitute therefor while the plant is grown.

4. The method according to claim 2, wherein the application of the xyloglucan-oligosaccharide to the plant is carried out by sprinkling a xyloglucan-oligosaccharide while the plant is grown.

5. The method according to claim 2, wherein the application of the xyloglucan-oligosaccharide to the plant is carried out by coating a seed of the plant with a xyloglucan-oligosaccharide.

6. The method according to claim 2, wherein the application of the xyloglucan-oligosaccharide to the plant is carried out by coating the plant itself with a xyloglucan-oligosaccharide.

7. The method according to claim 2, wherein the application of the xyloglucan-oligosaccharide to the plant is carried out by way of preparing a capsule of a synthetic seed by coating a mixture of an adventive embryo of the plant and the xyloglucan-oligosaccharide with a water-soluble polymer.

* * * * *